(12) United States Patent
Grady, Jr. et al.

(10) Patent No.: US 7,776,076 B2
(45) Date of Patent: Aug. 17, 2010

(54) BONE PLATE

(75) Inventors: Mark P. Grady, Jr., West Chester, PA (US); Keith A. Mayo, Gig Harbor, WA (US); Jeff W. Mast, Reno, NV (US); Brett R. Bolhofner, St. Petersburg, FL (US); Kenny Koay, West Chester, PA (US)

(73) Assignee: Synthes USA, LLC, West Chester, PA (US)

( * ) Notice: Subject to any disclaimer, the term of this patent is extended or adjusted under 35 U.S.C. 154(b) by 490 days.

(21) Appl. No.: 10/851,849

(22) Filed: May 21, 2004

(65) Prior Publication Data

US 2005/0261688 A1 Nov. 24, 2005

Related U.S. Application Data

(63) Continuation-in-part of application No. 10/843,113, filed on May 11, 2004.

(51) Int. Cl.
*A61B 17/80* (2006.01)
(52) U.S. Cl. .................. 606/291; 606/286; 606/319
(58) Field of Classification Search .............. 606/69, 606/70, 71, 280, 286, 289, 291, 319
See application file for complete search history.

(56) References Cited

U.S. PATENT DOCUMENTS

| | | | |
|---|---|---|---|
| 3,552,389 A | 1/1971 | Allgower et al. | 128/92 |
| 3,668,972 A | 6/1972 | Allgower et al. | 90/11 C |
| 3,716,050 A | 2/1973 | Johnston | 128/92 |
| 3,779,240 A | 12/1973 | Kondo | 128/92 |
| RE28,841 E | 6/1976 | Allgower et al. | 128/92 |
| 4,219,015 A | 8/1980 | Steinemann | 128/92 |
| 4,408,601 A | 10/1983 | Wenk | 128/92 D |
| RE31,628 E | 7/1984 | Allgower et al. | 128/92 |
| 4,493,317 A | 1/1985 | Klaue | 128/92 |
| 4,513,744 A | 4/1985 | Klaue | 128/92 |

(Continued)

FOREIGN PATENT DOCUMENTS

CH 611147 5/1979

(Continued)

OTHER PUBLICATIONS

ACE Symmetry™ Titanium Upper Extremity Plates, Ace Medical Company, (1996).

*Primary Examiner*—Eduardo C Robert
*Assistant Examiner*—Ellen C Hammond
(74) *Attorney, Agent, or Firm*—Fay Kaplun & Marcin, LLP

(57) ABSTRACT

A bone plate has an upper surface, a lower surface, and at least one first hole extending through the upper and lower surfaces. The first hole has two or three vertically separate regions, each region communicating with or abutting an adjacent region. The first hole has a first unthreaded upper region, which has a curved inward taper from the plate's upper surface toward the plate's lower surface. The first hole has a second threaded middle region, which has a conical inward taper from the plate's upper surface toward the plate's lower surface. A third unthreaded lower region has a conical outward taper from the plate's upper surface toward the plate's lower surface. The bone plate may be straight, curved, or include a combination of both straight and curved segments.

73 Claims, 11 Drawing Sheets

U.S. PATENT DOCUMENTS

| | | | |
|---|---|---|---|
| 4,565,193 A | 1/1986 | Streli | 128/92 D |
| 4,838,252 A | 6/1989 | Klaue | 128/92 YP |
| 4,927,421 A | 5/1990 | Goble et al. | 606/73 |
| 4,957,497 A | 9/1990 | Hoogland et al. | 606/71 |
| 4,988,350 A | 1/1991 | Herzberg | 606/65 |
| 5,002,544 A | 3/1991 | Klaue et al. | 606/69 |
| 5,006,120 A | 4/1991 | Carter | 606/69 |
| 5,041,114 A | 8/1991 | Chapman et al. | 606/62 |
| 5,085,660 A | 2/1992 | Lin | 606/73 |
| 5,129,901 A | 7/1992 | Decoste | 606/65 |
| 5,147,363 A * | 9/1992 | Harle | 606/73 |
| 5,151,103 A | 9/1992 | Tepic et al. | 606/69 |
| 5,190,544 A | 3/1993 | Chapman et al. | 606/69 |
| 5,197,966 A | 3/1993 | Sommerkamp | 606/69 |
| 5,269,784 A | 12/1993 | Mast | 606/69 |
| 5,275,601 A | 1/1994 | Gogolewski et al. | 606/72 |
| 5,304,180 A | 4/1994 | Slocum | 606/69 |
| 5,324,290 A | 6/1994 | Zdeblick et al. | 606/61 |
| 5,364,398 A | 11/1994 | Chapman et al. | 606/69 |
| 5,364,399 A | 11/1994 | Lowery et al. | 606/69 |
| 5,531,746 A | 7/1996 | Errico et al. | |
| 5,601,553 A | 2/1997 | Trebing et al. | 606/61 |
| 5,702,399 A | 12/1997 | Kilpela et al. | 606/72 |
| 5,709,686 A * | 1/1998 | Talos et al. | 606/69 |
| 5,810,823 A | 9/1998 | Klaue et al. | 606/69 |
| 5,938,664 A | 8/1999 | Winquist et al. | 606/69 |
| 5,954,722 A * | 9/1999 | Bono | 606/61 |
| 6,183,475 B1 | 2/2001 | Lester et al. | 606/69 |
| 6,206,881 B1 | 3/2001 | Frigg et al. | 606/69 |
| 6,322,562 B1 | 11/2001 | Wolter | 606/69 |
| 6,364,882 B1 | 4/2002 | Orbay | 606/69 |
| 6,440,135 B2 | 8/2002 | Orbay et al. | 606/69 |
| 6,454,770 B1 * | 9/2002 | Klaue | 606/281 |
| 6,527,776 B1 | 3/2003 | Michelson | 606/70 |
| D479,331 S * | 9/2003 | Pike et al. | D24/155 |
| 6,623,486 B1 | 9/2003 | Weaver et al. | 606/69 |
| 6,669,701 B2 | 12/2003 | Steiner et al. | 606/69 |
| 6,767,351 B2 * | 7/2004 | Orbay et al. | 606/287 |
| 6,955,677 B2 * | 10/2005 | Dahners | 606/287 |
| 7,179,260 B2 * | 2/2007 | Gerlach et al. | 606/69 |
| 7,527,639 B2 * | 5/2009 | Orbay et al. | 606/287 |
| 2002/0128654 A1 * | 9/2002 | Steger et al. | 606/69 |
| 2004/0049193 A1 * | 3/2004 | Capanni | 606/69 |
| 2004/0097937 A1 * | 5/2004 | Pike et al. | 606/69 |
| 2004/0254579 A1 * | 12/2004 | Buhren et al. | 606/71 |
| 2005/0165400 A1 * | 7/2005 | Fernandez | 606/69 |
| 2005/0216001 A1 * | 9/2005 | David | 606/61 |
| 2005/0277937 A1 * | 12/2005 | Leung et al. | 606/69 |
| 2006/0264946 A1 * | 11/2006 | Young | 606/69 |

FOREIGN PATENT DOCUMENTS

| | | |
|---|---|---|
| DE | 43 41 980 A | 6/1995 |
| DE | 43 43 117 A | 6/1995 |
| DE | 4438264 A1 | 3/1996 |
| DE | 93 21 544 U1 | 10/1999 |
| DE | 19858889 | 6/2000 |
| EP | 0 207 884 A2 | 1/1987 |
| EP | 1 468 655 A2 | 10/1999 |
| FR | 2233973 | 1/1975 |
| FR | 2405062 | 5/1979 |
| FR | 2405705 | 5/1979 |
| FR | 2405706 | 5/1979 |
| FR | 2496429 | 5/1979 |
| SU | 1279626 A1 | 12/1986 |
| WO | WO 97/09000 | 3/1997 |
| WO | WO 0053110 | 9/2000 |
| WO | WO 0053111 | 9/2000 |
| WO | 2004/107957 | 12/2004 |

* cited by examiner

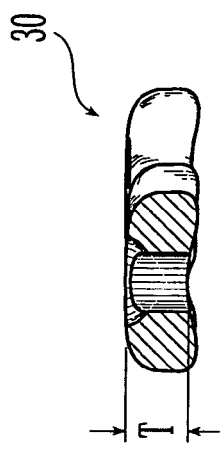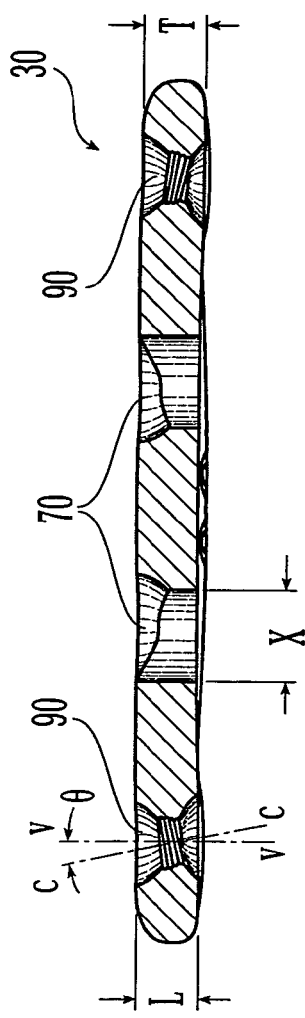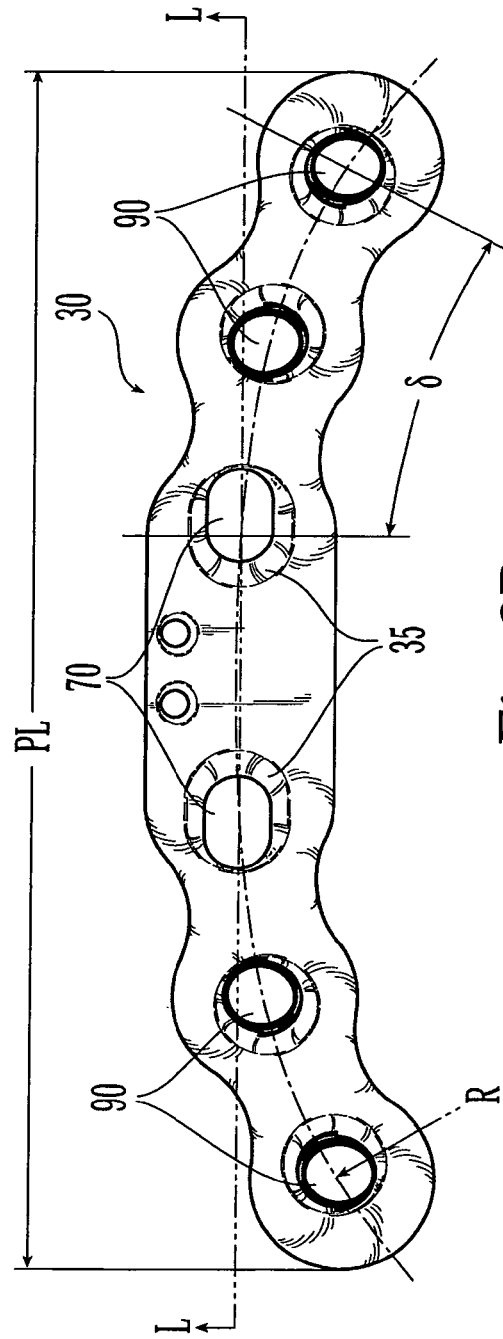
Fig. 2A
Fig. 2C
Fig. 2B

BONE PLATE

CROSS-REFERENCE TO RELATED APPLICATIONS

The present application is a continuation-in-part of U.S. patent application Ser. No. 10/843,113, filed on May 11, 2004, currently pending. The entire contents of this application is expressly incorporated herein by reference thereto.

FIELD OF THE INVENTION

The present invention relates generally to devices for bone fracture fixation and more specifically, to bone plates and systems for stabilization and/or compression of bone fractures.

BACKGROUND OF THE INVENTION

The use of bone plate and screw systems for treatment of bone fractures is widespread. Conventional bone plate and screw systems promote healing of a fracture by compressing the fracture ends together and drawing the bone fragments into close apposition with each other. If the plate is not provided with the appropriate hole types adapted to receive the proper screw types, then the angular relationships between the plate and screws may change postoperatively. This can lead to malalignment and poor clinical results.

Among the various different types of bone plate holes that are known in the art are the two different types of holes described below, each hole primarily intended for use with a different type of bone screw.

The first type of hole is a non-threaded relatively smooth hole, through which a screw with a smooth (non-threaded) head is inserted. These screws do not lock with the bone plate and are thus referred to as "non-locking" screws. Because non-locking screws do not lock with the plate hole, non-locking screws are not limited to a fixed angle with respect to the plate, but rather can be inserted at numerous angles. Inserting non-locking screws through the non-threaded plate holes and threading them into the bone effectively provides the desired compression of fracture ends.

The second type of hole is an internally threaded hole, which is adapted to mate with a screw having an externally threaded head. The threaded-head or "locking" screw is inserted at a fixed, predetermined angular relationship (determined by the central axis of the threaded hole) with respect to the bone plate. Locking screws, when mated with threaded bone-plate holes, possess high resistance to shear and torsional forces. Locking screws therefore resist loosening and thereby ensure stability between the screw and the bone plate.

Bone plates having both of the aforementioned types of holes are therefore desirable and are well known. Surgeons are limited, however, by the manufacturers' placement of the varying holes on a given bone plate. A surgeon can achieve optimal compression when using a screw (e.g., a non-locking screw) without locking it to the plate. A surgeon can achieve desired stability between the screw, plate, and bone when using a locking screw with an internally-threaded hole.

It would thus be advantageous for a hole in a bone plate to be adapted to receive, at the surgeon's election, either non-locking screws for obtaining optimal compression or locking-screws for obtaining optimal stability, while minimizing any compromise in the strength of the bone plate.

SUMMARY OF THE INVENTION

The bone plate of present invention is a bone plate used for bone fracture fixation. Various embodiments of a bone plate having coaxial combination holes are described.

Among the various different types of bone plate holes that are known in the art are threaded holes and non-threaded holes. "Locking" screws (screws with threaded heads) are typically used with threaded holes. Locking screws, when mated with threaded holes, possess high resistance to shear and torsional forces and therefore ensure stability between the screw and bone plate. "Non-locking" screws are typically used with unthreaded holes and, unlike locking screws that mate with threaded holes, may be inserted at any one of a number of angles. Non-locking screws provide optimal compression of fractured ends.

A coaxial combination hole is, at once, adapted to receive (and utilize the benefits of) either a locking screw or non-locking screw. A coaxial combination hole is a hole which is threaded only partially through its length. In one preferred embodiment, the hole has a generally circular cross section with varying hole diameter. In a preferred embodiment, the hole has three regions: an upper region, a middle region, and a lower region. The upper region may be unthreaded and may have, in a direction from the plate's upper surface to its lower surface, a curved inward taper. The middle region may be threaded and may have, in a direction from the plate's upper surface to its lower surface, a conical inward taper. The lower region may be unthreaded and may have, in a direction from the plate's upper surface to its lower surface, an outward taper.

It will be appreciated that either type of the aforementioned screws may be used (and produce its intended results) with a coaxial combination hole. The threaded head of a threaded-head screw may mate with threaded middle region of the hole. Alternatively, a screw with an unthreaded head (or even a screw with a threaded head) may be inserted through a coaxial combination hole, without any mating of any threads, at any one of a number of angles. The outward taper of the coaxial combination hole's lower region provides room for the screw's shaft to be inserted at an angle (with respect to the center of the hole). Likewise the curved inward taper of the upper region of the hole provides a seat for the screw head to rest in, even when the screw is inserted at an angle. It will be appreciated, then, that at any given coaxial combination hole, a surgeon may elect to use either a screw for screw-plate stability or a screw for compression of fracture ends.

Coaxial combination holes may be placed in any type of bone plate. Coaxial combination holes provide multiple options for the surgeon. And because the holes do not require a larger cavity in the bone plate than would otherwise be necessary for an ordinary hole, the strength, size, and integrity of the bone plate are not compromised. Coaxial combination holes are therefore particularly useful in relatively small bone plates (e.g., pubic symphysis plates).

A coaxial combination hole has a central axis and a vertical axis. The hole's vertical axis is perpendicular to the plane formed by the plate's upper surface (if the plate has a straight upper surface), or to the plane that is tangential to the pinnacle of the plate's upper surface (if the plate is convex). A hole may have a central axis that is parallel to its vertical axis, or that is not parallel to its vertical axis (thereby biasing the shaft of the screw in one direction or another). A plate may have holes with any combination of foregoing hole orientations.

In preferred embodiments, bone plates have between 4 and 8 holes. In some embodiments, all plate holes are coaxial combination holes. In other embodiments, the bone plates may have some coaxial combination holes and at least one of another of a number of types of holes. One example of another type of hole is a dynamic compression ("DC") hole. A dynamic compression hole may be an elongated hole having an oblique portion or ramp having an inclination such that when the ramp is engaged by the underside of the head of a screw, the bone plate is displaced in a direction to move the ramp away from the non-locking screw, causing the plate to apply a pressure to hold the fracture ends in contact or in tight engagement. Another example of another type of hole is a non-coaxial combination hole. A non-coaxial combination hole may be an elongated hole having a portion of its perimeter threaded and another portion of its perimeter unthreaded. In addition to, or in lieu of, the foregoing two examples, other types of holes may be formed in a bone plate having coaxial combination holes.

In one embodiment of the bone plate, the plate has a longitudinal axis, and has a straight center portion and curved ends. In one embodiment, the plate has two holes in the straight portion and two holes in each of the curved end portions. In one embodiment of this plate, all six holes may be coaxial combination holes. In another embodiment of this plate, the two holes on the straight portion may be either DC holes or non-coaxial combination holes, and the four holes on the curved end portions may be coaxial combination holes. In one embodiment of this plate, the width of the bone plate is narrower where there are no holes than where there are holes.

In another embodiment of the bone plate, the plate has a longitudinal axis and is straight. In one embodiment, the plate may have only coaxial combination holes, all of which may lie along the plate's longitudinal axis.

In another embodiment of the bone plate, the entire plate may be curved. In one embodiment, the plate may have only coaxial combination holes, all of which may lie along the plate's longitudinal axis (which runs along the center of the plate's width).

In the various embodiments, the plate's upper and lower surfaces may be straight or curved. In a preferred embodiment, the plate's upper surface may be convex, while the plate's lower surface may be concave.

BRIEF DESCRIPTION OF THE DRAWINGS

These figures represent preferred embodiments of the present invention. Those skilled in the art will recognize that numerous variations and modifications may be made without departing from the scope of the present invention. Accordingly, it should be understood that these figures are not intended as limitations on the scope of the invention, which is defined only by the claims.

FIG. 2A is a side cross-sectional view of a second embodiment of a bone plate having coaxial combination holes and having dynamic compression holes.

FIG. 2B is a plan view of the bone plate of FIG. 2A.

FIG. 2C is a cross-sectional view of the bone plate of FIG. 2A taken along the cross section B-B.

DESCRIPTION OF THE PREFERRED EMBODIMENTS

The present invention is described below with reference to the preferred embodiments. Those skilled in the art will recognize that numerous variations and modifications may be made without departing from the scope of the present invention. Accordingly, it should be understood that the embodiments of the invention described below are not intended as limitations on the scope of the invention, which is defined only by the claims.

Figure 1C:
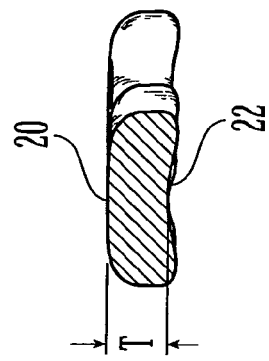
FIG. 1C is a cross-sectional view of the bone plate of FIG. 1A taken along the cross section B-B.
Figure 1A:
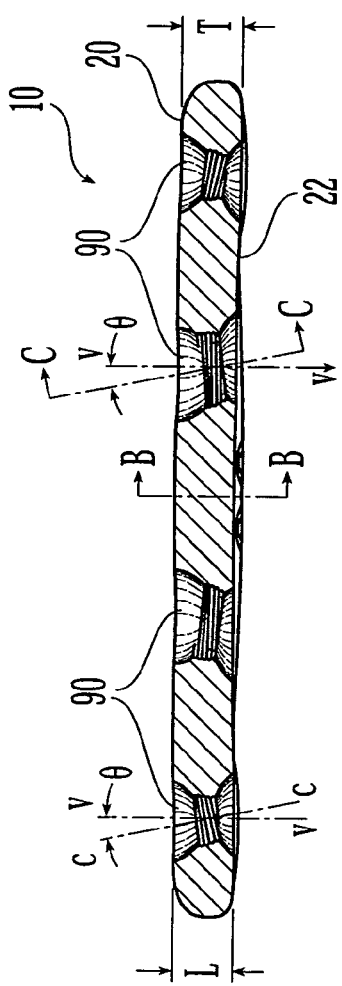
FIG. 1A is a side cross-sectional view of a first embodiment of a bone plate having coaxial combination holes.
Figure 3A:
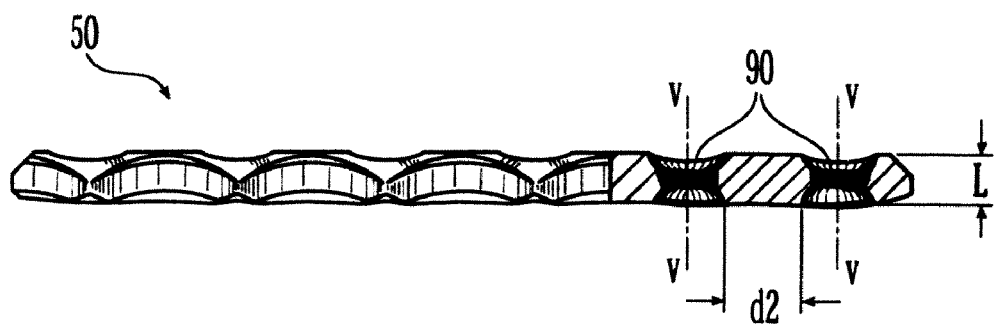
FIG. 3A is a third embodiment of a bone plate having coaxial combination holes.

Reference is now made to FIGS. 1A, 2A, and 3A, which illustrate side, cross-sectional views of various embodiments of a bone plate. The bone plates may have at least one coaxial combination hole 90, which has a length L that extends from the upper surface of the bone plate to the lower surface of the bone plate. The coaxial combination hole 90 is threaded only partially through the hole's length L. As such, with a given coaxial combination hole, a surgeon may elect to: (1) thread a screw having a thread on at least a portion of its head into and through the hole; or (2) insert a screw having an unthreaded head through the hole and into the bone. In a preferred embodiment, the hole 90 has length L of approximately 3.4 mm to 4.0 mm, which preferably corresponds to the thickness T of the bone plate.

Figure 1B:
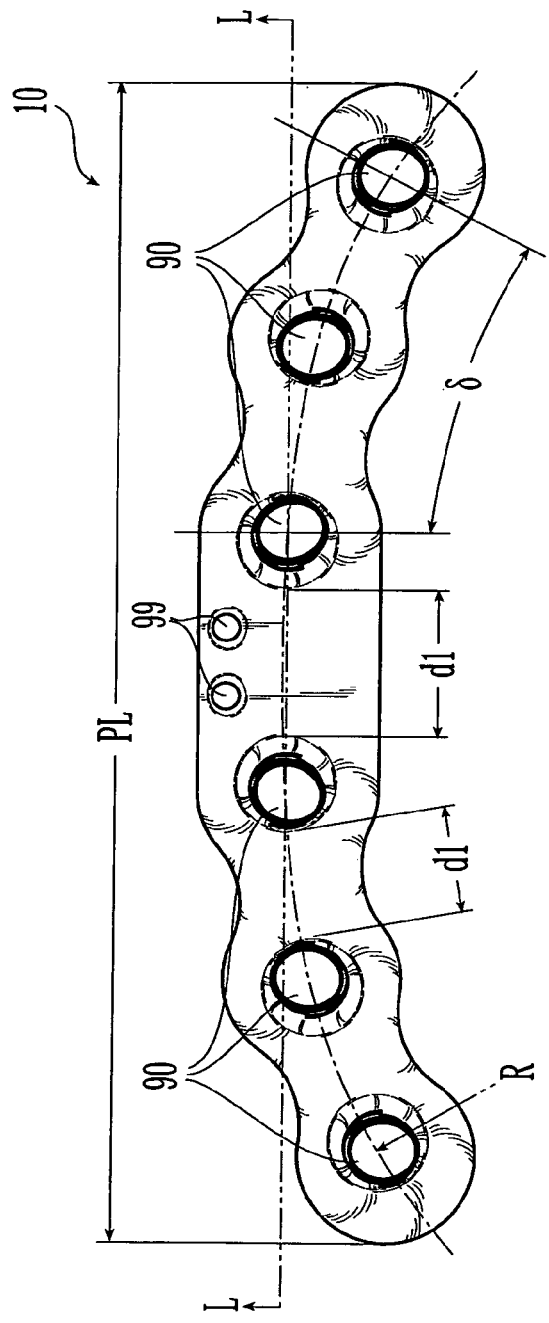
FIG. 1B is a plan view of the bone plate of FIG. 1A.
Figure 3B:
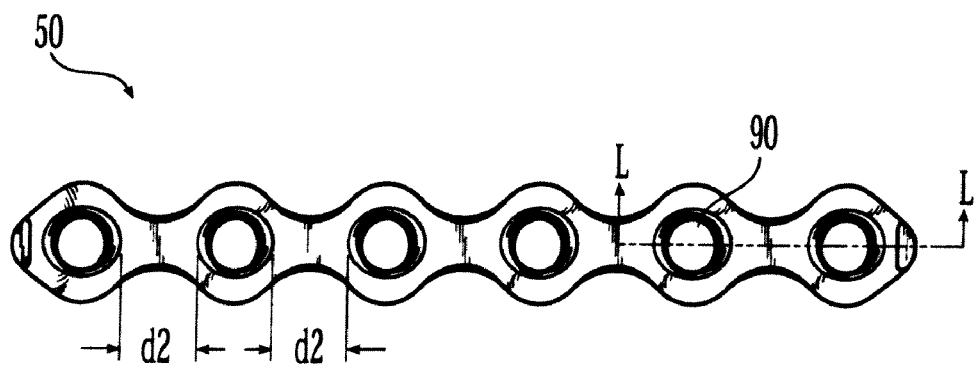
FIG. 3B is a plan view of the bone plate of FIG. 3A.

Reference is now made to FIGS. 1B, 2B, and 3B, which illustrate plan views of various embodiments of the bone plate having at least one coaxial combination hole 90. Each bone plate may have at least a central region with a longitudinal axis L-L. Each bone plate hole 90 may have a vertical axis V-V, which is perpendicular to the plane on which the plate's upper surface lies (if the plate has a straight upper surface), or to the plane that is tangential to the pinnacle of the plate's upper surface (if the plate is convex). (See FIGS. 1A, 2A, and 3A.)

Reference is now made to FIGS. 1C and 2C, which illustrate cross-sectional views of the bone plates along the respective cross sections B-B. In a preferred embodiment, the upper surface of the plate may be convex and the lower surface of the plate may be concave, as shown in FIGS. 1C and 2C. In a preferred embodiment, the radius of curvature for both surfaces may be from about 15 mm to about 35 mm, and preferably about 25 mm. In another embodiment, one or both of the plate surfaces may be flat.

As shown in FIG. 1A, hole 90 may extend from the upper surface 20 to the lower surface 22 of the bone plate 10. In one embodiment, the diameters of the hole 90 at its uppermost surface and its lower most surface may be equal or close to equal. The hole 90 may be widest at the uppermost surface 20 and lowermost surface 22 of the plate 10. Each hole 90 may have a central axis C-C. (See FIGS. 1A and 2A.) In some embodiments of the hole 90, the central axis C-C of hole 90 may be parallel to the vertical axis V-V, as shown in FIG. 3A (central axis C-C not shown). In other embodiments, the central axis C-C of hole 90 will intersect with the vertical axis V-V at an angle $\theta$, as shown in FIGS. 1A and 2A. In preferred embodiments, the angle $\theta$ may vary from about 3° to about 17°, although other angles are contemplated.

Figure 4A:
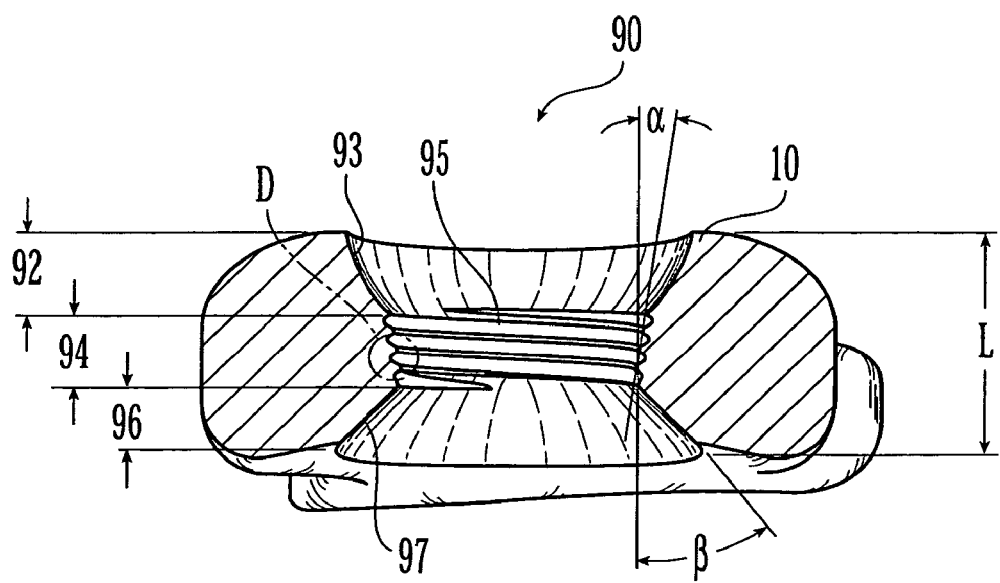
FIG. 4A is a cross-sectional view of one embodiment of a coaxial combination hole.

As shown in FIG. 4A, the hole 90 may have three regions: an upper region 92, a middle region 94, and a lower region 96. The upper region 92 of the hole 90 may have an unthreaded inner surface 93 which, is preferably smooth, although texturing may be provided. In a preferred embodiment, the upper region 92 may have a curved inward taper, preferably concave, more preferably spherical, from the top surface of the plate to where the upper region 92 of the hole 90 meets the middle region 94. The upper region 92 of the hole 90 is preferably narrowest where it meets the middle region 94. Preferably, the upper region is approximately 1.0 mm to approximately 1.2 mm in length (along the axis C-C). In a preferred embodiment, the upper region may comprise about 25% to about 35% of the thickness T of the plate. In one embodiment, the diameter of the upper region 92, at the region's broadest point, may be about 6 mm and, at the region's narrowest point, may be about 4 mm. In another embodiment the diameter of the upper region 92, at the region's broadest point, may be about 8 mm and, at the region's narrowest point, may be about 6 mm.

Figure 4B:
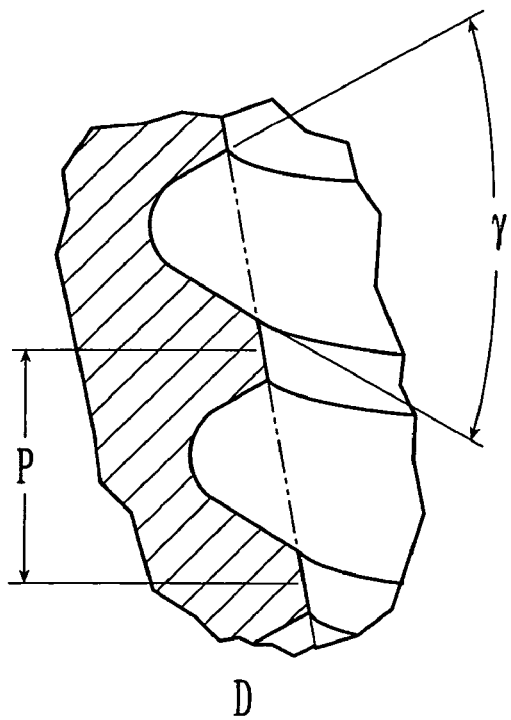
FIG. 4B is a magnified view of a portion of the thread of the coaxial combination hole of FIG. 4A.

The middle region 94 of the hole 90 may have a threaded inner surface 95. In one embodiment, the threads have a pitch P (as shown in FIG. 4B, which is a magnified partial view of the threaded surface 95) of approximately 0.3 mm to 0.5 mm. In a preferred embodiment, the thread angle $\gamma$ may be approximately 50° to 70°, and preferably about 60°. In a preferred embodiment, the threaded region has at least one thread revolution, and preferably about three thread revolutions. Referring again to FIG. 4A, the threaded inner surface 95 may, in a direction from the upper surface to the lower surface, have a conical inward taper. In a preferred embodiment, the threaded inner surface 95 may taper at an angle $\alpha$ of approximately 5° to 15°, and preferably approximately 10°. The middle region 94 may be the narrowest region (i.e., smallest-diameter region) of the hole 90. In a preferred embodiment, the middle region 94 may be approximately 1.5 mm to approximately 1.9 mm in length (along the axis C-C). In a preferred embodiment, the middle region 94 may comprise about 40% to 50% of the thickness T of the plate. In one embodiment, the diameter of the middle region 94 may vary only slightly (due to the relatively shallow conical taper) and may be about 4 mm or, in another embodiment, about 6 mm. The diameter or taper of the middle region 94 may of course vary depending upon the size and/or taper of the screw.

The lower region 96 of the hole 90 may have an unthreaded inner surface 97 which is preferably smooth, although texturing may be provided. In a preferred embodiment, the lower region 96 may, from where it meets the middle region 94 to the lower surface of the plate, have a conical outward taper. In a preferred embodiment, the lower region 96 may taper outwardly at an angle $\beta$ of approximately 35° to 55°, and preferably approximately 45°. In a preferred embodiment, the lower region 96 may be approximately 0.8 mm to approximately 1.2 mm in length (along the axis C-C). In a preferred embodiment, the lower region 96 may comprise about 20% to 35% of the thickness T of the plate. In one embodiment, the diameter of the lower region 96, at the region's narrowest point, may be about 4 mm and, at the region's broadest point, may be about 6 mm. In another embodiment, the diameter of the lower region 96, at the region's narrowest point, may be about 6 mm and, at the region's broadest point, may be about 8 mm.

Figure 5:
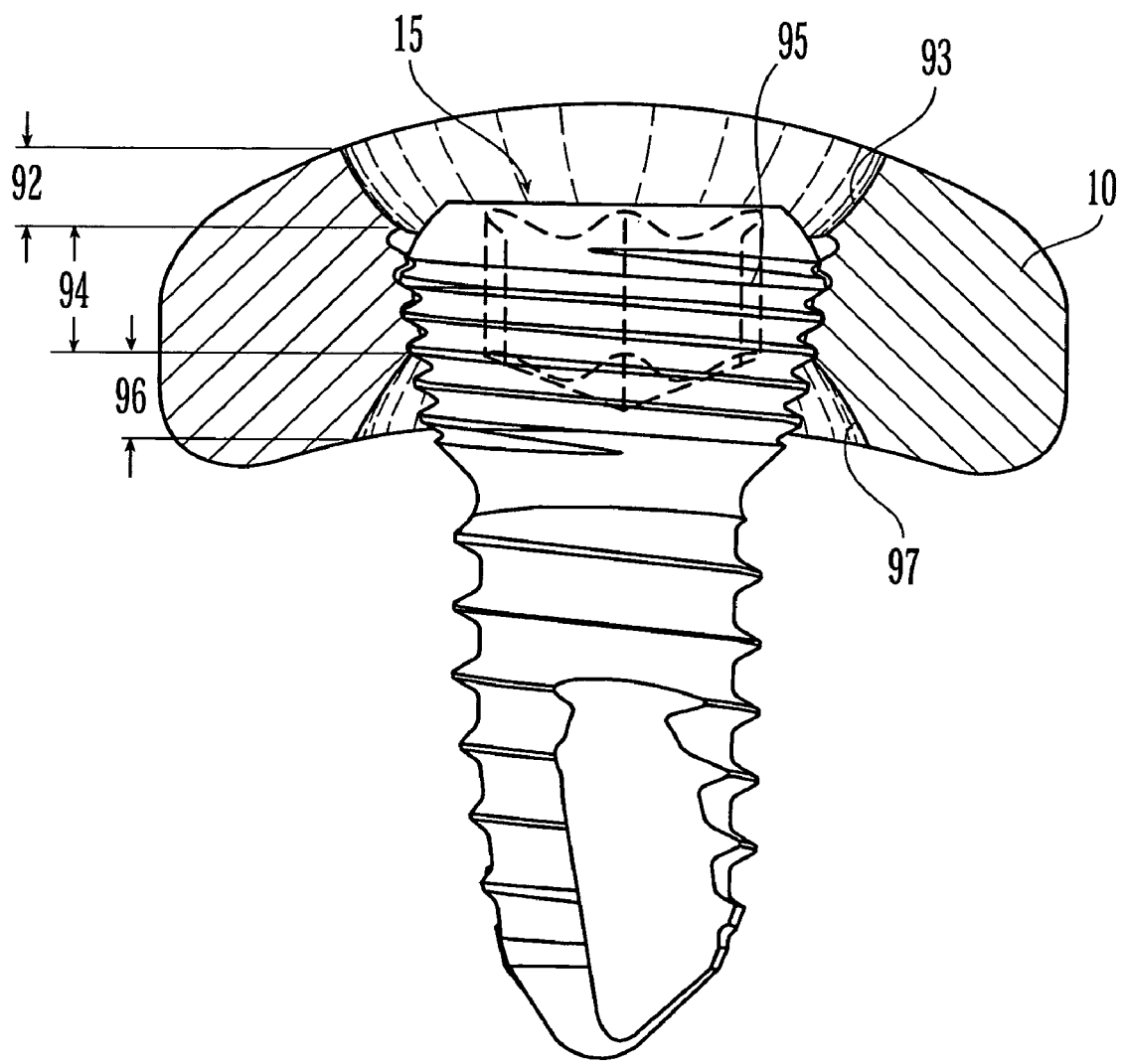
FIG. 5 is a cross-sectional view of a screw, having a threaded head, inserted through a coaxial combination hole.
Figure 9:
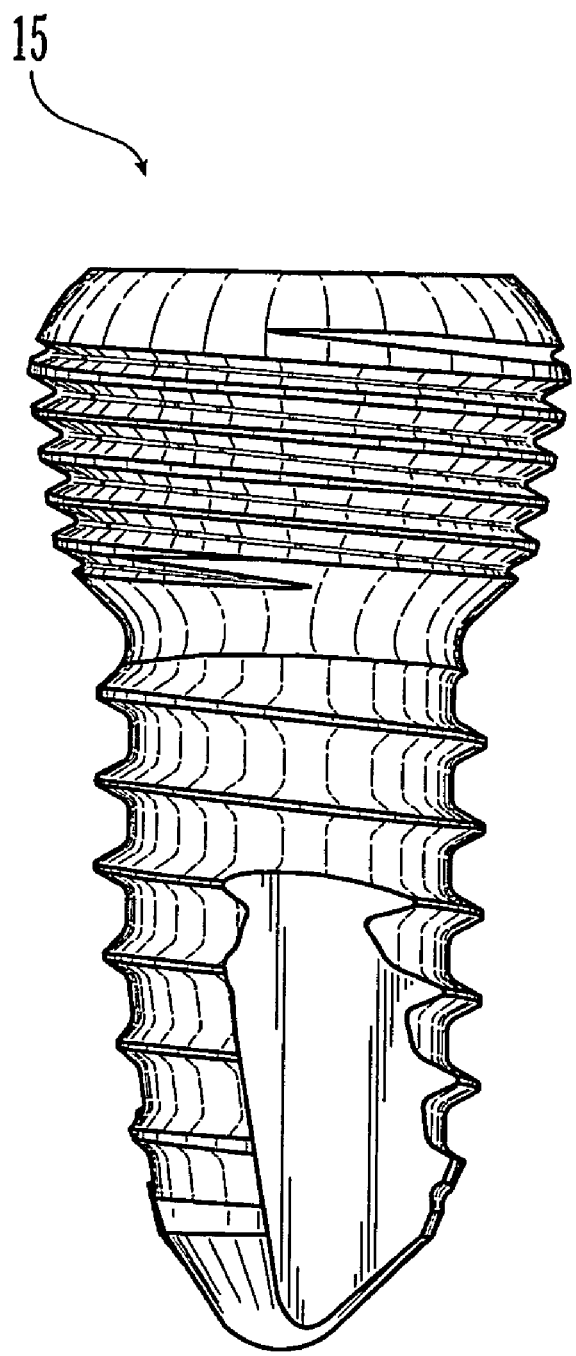
FIG. 9 is a side view of one embodiment of a screw that has a conically-tapered threaded head.

Different types of screws may be used with the hole 90. One type of screw is a screw that has a conically-tapered threaded head (shown in FIG. 9). As shown in FIG. 5, the external threads of the screw's head may mate with the internal threads 95 of the middle region 94 of the hole 90. This threaded-head screw 15 may be inserted at only one angle (with respect to the plate), which may be fixed by the threads 95 in the plate 10.

Figure 6A:
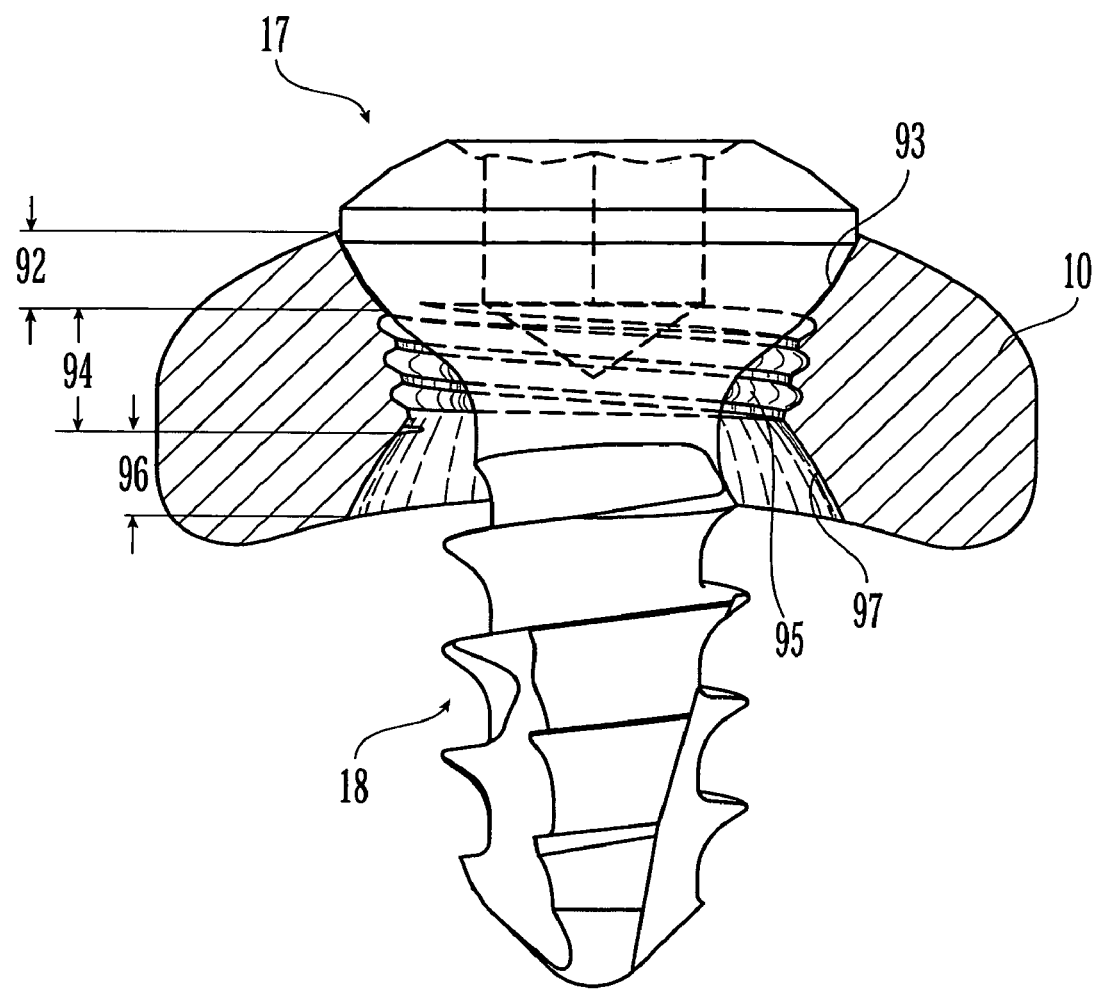
FIG. 6A is a cross-sectional view of a screw, having a non-threaded head, inserted through a coaxial combination hole at one angle.
Figure 6B:
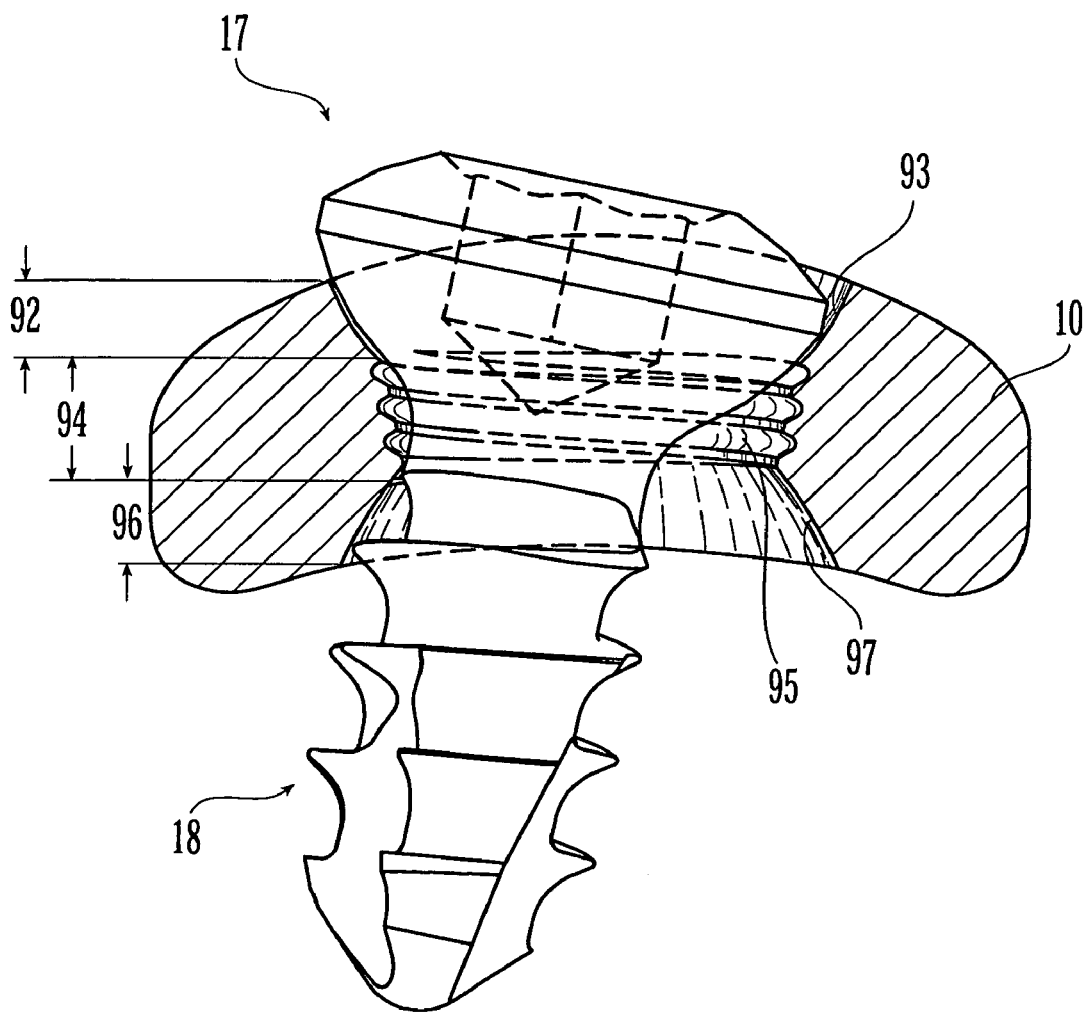
FIG. 6B is a cross-sectional view of a unthreaded-head screw inserted through a coaxial combination hole at an angle different from that of the screw of FIG. 6A.
Figure 10:
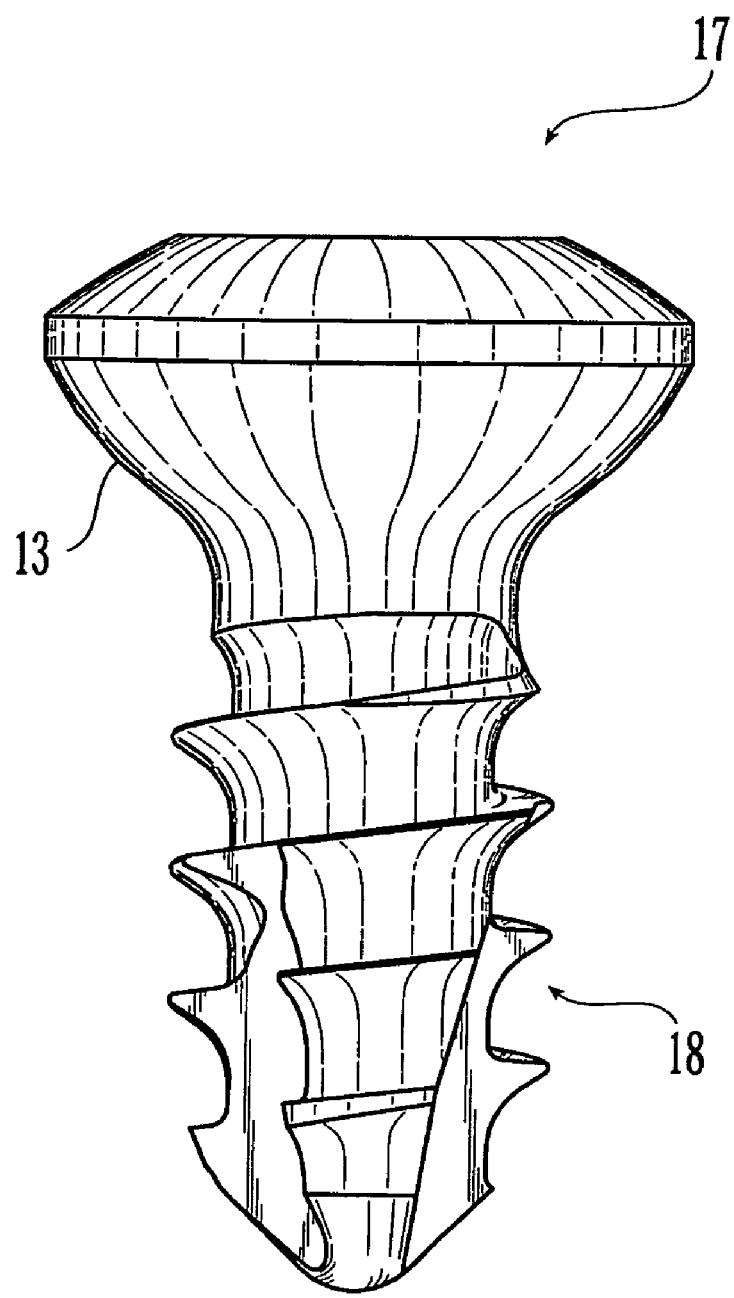
FIG. 10 is a side view of one embodiment of a screw having an unthreaded head.

A second type of screw that may be used with the hole 90 is a screw with a threaded shaft, but with an unthreaded head (shown in FIG. 10). An unthreaded-head screw may be inserted into hole 90 at any one of a number of angles. FIG. 6A illustrates an unthreaded-head screw 17 inserted at an angle substantially perpendicular to the longitudinal axis of the plate 10. FIG. 6B illustrates an unthreaded-head screw 17 inserted at a non-perpendicular angle with respect to the plate 10. The conical outward taper (shown at surface 97) of the lower region 96 of the hole 90 provides room for screw shaft 18 to be inserted at an angle with respect to the center of the hole 90. Likewise, the curved inward taper of the upper region 92 of the hole 90 provides a seat (at surface 93) for the screw head to rest in when an unthreaded-head screw 17 is inserted at an angle. A threaded-head screw may be used with a coaxial combination hole 90 in the same manner as the aforementioned unthreaded-head screw 17.

Although virtually any type of bone plate may benefit from coaxial combination holes 90, coaxial combination holes are particularly useful for pubic symphysis plates and other relatively small bone plates. (The pubic symphysis is the connection between the two halves of the pubis and may be damaged as a result of an accident.) Because a surgeon may elect to use either a locking screw or a non-locking compression screw with a coaxial combination hole, a bone plate having a coaxial combination hole may be more versatile than plates having other types of holes. The benefits may include: (1) a reduced need to manufacture many different plates having varying hole arrangement patterns; and (2) enhancement of clinical results. Because a coaxial combination hole does not require a substantially larger cavity in the bone plate than would otherwise be necessary for a simple hole, a coaxial combination hole provides desired flexibility for the surgeon without unduly compromising the strength, size, or integrity of the bone plate. Plates having coaxial combination holes may thus find particular utilization in pubic symphysis plates and other relatively small bone plates.

In one embodiment, the bone plate of the present invention may be a pubic symphysis plate as shown in FIG. 1B, and may have a plurality of holes, all of which may be coaxial combination holes 90. In one embodiment, the plate may have a length PL of approximately 70 mm to 90 mm. In one embodiment, the plate may have curved ends, as shown in FIG. 1B, with a radius of curvature R. In a preferred embodiment, two coaxial combination holes 90 are located on the straight center portion of the plate. In a preferred embodiment, the plate ends may curve approximately at a 45 mm-55 mm radius R, spanning a 25°-35° angle $\delta$. Preferably two coaxial combination holes 90 are placed along an arcs (on both sides of the plate's straight center portion) having a radius of curvature of about 50 mm. In a preferred embodiment, the hole 90 on the curved portion adjacent to the hole 90 on the straight portion is located approximately 12°-18° on the arc away from the hole 90 on the straight portion. Likewise, the two holes 90 on either curved portion may be placed along an arc approximately 12°-18° apart from each other. In a preferred embodiment, the plate may be symmetrical from one side to the other (i.e., a mirror hole arrangement on the other side of the plate is contemplated). In a preferred embodiment, the two holes near the center of the plate may lie along the longitudinal axis L-L of the center region of the plate 10. The remaining holes may be offset from the longitudinal axis L-L, as shown in FIG. 1B.

In a preferred embodiment, the central axes C-C of the holes 90 are not parallel to the respective vertical axes V-V of the holes 90. In a preferred embodiment, as shown in FIG. 1A, the two holes near the center of the plate have central axes C-C oriented to bias the tips of the screws in a direction away from the center of plate. In a preferred embodiment, the angle θ between each of these two central axes C-C and the vertical axes V-V is approximately 8° to 15°. In a preferred embodiment, as shown in FIG. 1A, each of the holes 90, that are located near the ends of the plate, has a central axis C-C oriented to bias the tips of the screws in a direction towards the center of plate. In a preferred embodiment the angle θ between each of these central axes C-C and the vertical axes V-V is approximately 4° to 10°.

In a preferred embodiment, the linear plate-surface distance d1 between the edges of holes 90 may vary from hole to hole and may be approximately 10 mm to 12 mm. In a preferred embodiment, as shown in FIG. 1B, there may be necking of the plate surface in between hole locations (i.e., the webs between the holes may be narrowed). This necking serves to achieve a desired balance between plate strength and plate size: plate strength is maximized, while plate size is minimized. In another embodiment the width of the plate between holes may be the same as the width of the plate where the holes are located.

In a preferred embodiment, the plate may have at least one hole 99, preferably near the center of the plate. Holes 99 may aid in the placement of the plate onto the bone (e.g., for use with a guide wire) or may be provided as a suture hole.

Generally, for all embodiments, a shorter bone plate having only a few (e.g., 4) holes may be used when the fracture is relatively small or when the patient's bone or joint (e.g., pubic symphysis) being operated on is relatively small.

A plan view of a second embodiment of a pubic symphysis plate is shown in FIG. 2B. The primary difference between this embodiment and the foregoing embodiment (which is illustrated in FIGS. 1A and 1B) is that the two holes near the center of the plate 30 of this embodiment are dynamic compression ("DC") holes 70 instead of coaxial combination holes 90. This embodiment of a bone plate is particularly useful when, to bring parts closer together, "extra" compression is desired. The DC holes are substantially similar to those disclosed in the specifications of United States publication No. 2002/0045901, in U.S. Pat. No. 6,669,701, and in reissued U.S. Pat. No. RE. 31,628, the contents of which are incorporated herein by reference. As shown in FIG. 2B, DC hole 70 is elongated in a direction substantially aligned with the longitudinal axis L-L of the plate 30. As shown in FIG. 2B, DC hole 70 has an oblique portion or ramp 35 having an inclination such that when ramp 35 is engaged by the underside 13 of the head of a screw, preferably a screw having a head that is not threaded, and is preferably smooth and curved on the underside 13 which contacts the bone plate, the bone plate 30 is displaced in a direction to move ramp 35 away from the non-locking screw, causing the plate 30 to apply a pressure to hold the fracture ends in contact, preferably in engagement, along at least a portion of the fracture length. In a preferred embodiment, each of the holes 30 has a length X (illustrated in FIG. 2A) of approximately 6 mm to 7 mm.

Figure 7:
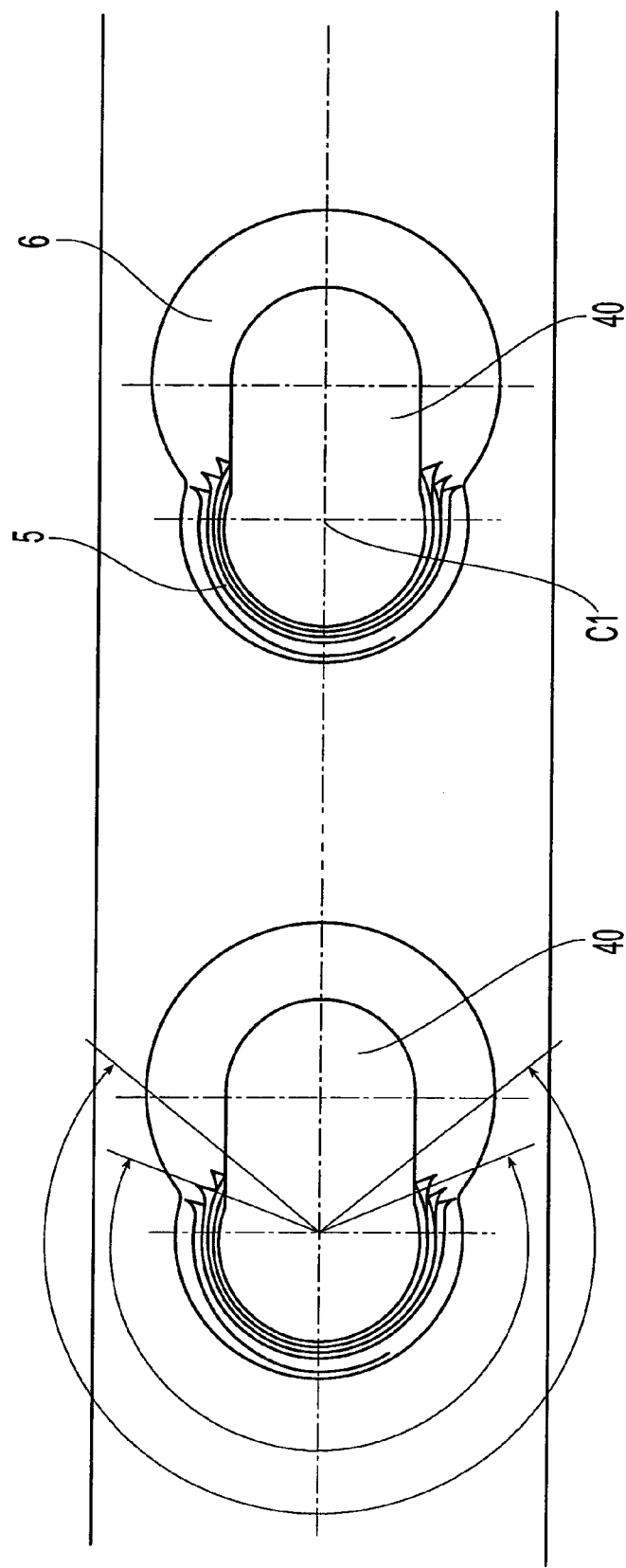
FIG. 7 is a plan view of a segment of a bone plate having non-coaxial combination holes.

Alternatively, the two holes near the center of the plate 30 may be non-coaxial combination holes 40 (instead of coaxial combination holes 90 or DC holes 70). The non-coaxial combination holes are substantially similar to those disclosed in the specifications of U.S. Pat. No. 6,669,701 and of United States publication No. 2002/0045901, the contents of which are hereby incorporated by reference. Reference is now made to FIG. 7. FIG. 7 illustrates a bone plate having a plurality of combination holes 40, which extend from the plate's upper surface to its lower surface. The holes 40 may be elongated (e.g., in a direction substantially aligned with a longitudinal axis of the plate) and may include a threaded portion 5 and a non-threaded portion 6. The threaded portion 5 may extend over a range of greater than about 180° with respect to a center point C1. The threaded portion 5 of the hole 40 may be dimensioned and configured to engage a threaded head portion of a threaded-head bone screw, and fix the bone screw at a predetermined angle with respect to the bone plate. Preferably, the threaded portion 5 of the hole 40 extends through the full thickness of the bone plate (i.e., from the plate's upper surface to its lower surface) thus maximizing the stability of the bone screw to bone plate interface. A threaded-head screw or a non-threaded head screw may (e.g., for compression) pass through the non-threaded portion 6 of a combination hole 40.

Another embodiment of a plate having coaxial combination holes is illustrated in FIGS. 3A and 3B. In one embodiment, the plate 50 may have a plurality of holes, all of which may be coaxial combination holes 90. Each of the holes 90 may lie along the longitudinal axis L-L of the plate 50. In one embodiment, the central axis C-C of each of the holes 90 may be parallel to the corresponding vertical axis V-V of each of the holes 90, as shown in FIG. 3A (central axis C-C not shown). In a preferred embodiment, the linear plate-surface distance d2 between the edges of holes 90 may be approximately 6 mm to 9 mm.

Figure 8:
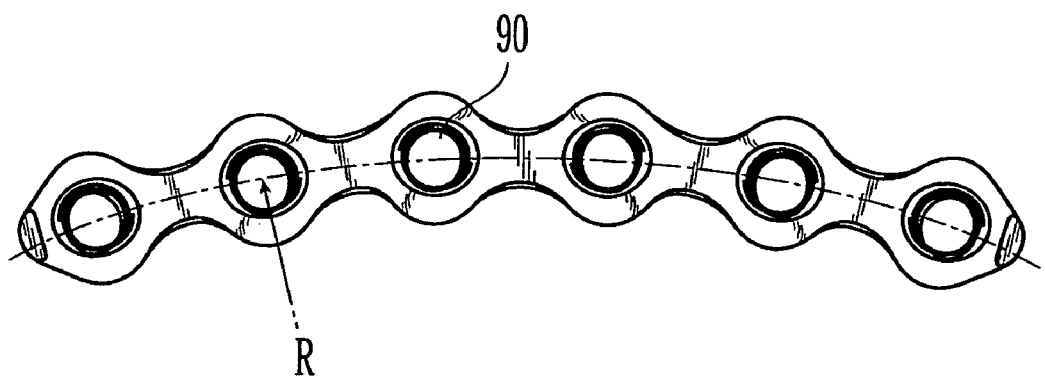
FIG. 8 is a plan view of the bone plate of FIGS. 3A and 3B, in a curved condition.

A variation on the aforementioned embodiment (illustrated in FIGS. 3A and 3B) is illustrated in FIG. 8. FIG. 8. is the bone plate of FIGS. 3A and 3B, in a "curved condition." Though the bone plate of FIGS. 3A and 3B may be formed of such material to allow a surgeon to preoperatively bend the plate into a desired shape, a bone plate manufactured to a bend condition may be desirable. In the human body, a ball-and-socket joint is formed by the two acetabula of the pelvis and the head of each femur. The bone plate of FIG. 9 may be especially useful for use on the posterior outer surface of a fractured acetabulum. The plate may have a radius of curvature R, which in a preferred embodiment, is about 100-115 mm.

While the present invention has been described with reference to the preferred embodiments, those skilled in the art will recognize that numerous variations and modifications may be made without departing from the scope of the present invention. Accordingly, it should be understood that the embodiments of the invention described above are not intended as limitations on the scope of the invention, which is defined only by the following claims.

What is claimed is:

1. A bone plate comprising a monolithic plate body having an upper surface and a lower surface, the monolithic plate body including a first hole extending therethrough from the upper surface to the lower surface, the hole including three regions separated from one another along a length of the first hole, first and third regions of the first hole being non-threaded, and a second middle region of the hole between the first and third regions including threading formed in a portion of the monolithic plate body forming a wall of the second region of the hole, the threaded second region being configured and dimensioned to lock a mating fastener therein along a single, fixed first hole axis wherein the second region is, in a direction from the upper surface to the lower surface, conically tapered inward, wherein the first region has, in a direction from the upper surface to the lower surface, an inward taper that is present around the axis of the hole.

2. The bone plate of claim 1, wherein the first region and the second region are in communication with one another.

3. The bone plate of claim 2, wherein a point of the first region nearest the lower surface abuts a point of the second region nearest the upper surface.

4. The bone plate of claim 1, wherein the first region is substantially smooth.

5. The bone plate of claim 1, wherein the inward taper is curved.

6. The bone plate of claim 5, wherein the curved inward taper is spherical.

7. The bone plate of claim 1, wherein the first hole has a substantially circular cross section with a diameter.

8. The bone plate of claim 7, wherein the diameter of the circular cross section varies along the first hole axis.

9. The bone plate of claim 1, wherein the second region conically tapers at a cone angle of between about 5° and 15°.

10. The bone plate of claim 1, wherein a maximum diameter of the first region is greater than a maximum diameter of the second region.

11. The bone plate of claim 1, wherein a minimum diameter of the first region is substantially equal to a maximum diameter of the second region.

12. The bone plate of claim 1, wherein the third region communicates with the second region.

13. The bone plate of claim 12, wherein a point of the second region nearest the lower surface abuts a point of the third region nearest the upper surface.

14. The bone plate of claim 13, wherein the third region is non-threaded.

15. The bone plate of claim 14, wherein the third region is substantially smooth.

16. The bone plate of claim 14, wherein the third region is, in a direction from the upper surface to the lower surface, tapered outward.

17. The bone plate of claim 16, wherein the outward taper of the third region is conical.

18. The bone plate of claim 16, wherein the third region conically tapers at a cone angle of between about 40° and 50°.

19. The bone plate of claim 16, wherein a maximum diameter of the third region is greater than a maximum diameter of the second region.

20. The bone plate of claim 16, wherein a minimum diameter of the third region is substantially equal to a minimum diameter of the second region.

21. The bone plate of claim 16, wherein a maximum diameter of the third region is substantially equal to a maximum diameter of the upper region.

22. The bone plate of claim 1, further comprising a second hole, different from the first hole, formed in the monolithic plate body.

23. The bone plate of claim 22, wherein the second hole is elongated in a direction substantially parallel to a plane containing the upper surface of the plate and extends through the upper and lower surfaces.

24. The bone plate of claim 23, wherein the second hole is non-threaded and has an outer perimeter, at least a portion of the outer perimeter tapering inward from the upper surface to the lower surface of the plate to form at least one ramp surface for engagement with a head of a mating fastener inserted therethrough.

25. The bone plate of claim 23, the second hole having a center point and wherein the second hole includes a threaded portion and a non-threaded portion, and the threaded portion extends through an angle of between about 190° and about 280° with respect to the center point.

26. The bone plate of claim 23, wherein the plate body defines a longitudinal axis, and the second hole is elongated in a direction that is substantially aligned with the longitudinal axis.

27. The bone plate of claim 26, wherein the plate comprises at least two first holes and at least two second holes.

28. The bone plate of claim 1, wherein the bone plate extends along a longitudinal axis.

29. The bone plate of claim 28, wherein the bone plate has a straight portion extending along the longitudinal axis and a first curved portion at a first end thereof.

30. The bone plate of claim 29, wherein the plate includes a first end and a second end substantially opposite the first end, the plate including a second curved portion at the second end with the straight portion located between the first and second curved portions.

31. The bone plate of claim 30, wherein the first curved portion has a radius of curvature between about 40 mm and about 60 mm.

32. The bone plate of claim 30, wherein two second holes are located adjacent to one another in the straight portion.

33. The bone plate of claim 32, wherein a first one of the first holes is located on the first curved portion, and a second one of the first holes is located on the second curved portion proximate the second end of the plate.

34. The bone plate of claim 33, wherein the first one of the first holes is located adjacent to a first one of the second holes.

35. The bone plate of claim 34, wherein the first one of the first holes and the first one of the second holes are separated by a distance of about 12° to about 18° on the curved portion.

36. The bone plate of claim 34, wherein the first one of the first holes is located adjacent to a second one of the first holes.

37. The bone plate of claim 36, wherein the first one of the first holes and the second one of the first holes are separated by a distance of about 12° to about 18° on the curved portion.

38. The bone plate of claim 1, wherein the first hole axis of the first hole is not parallel to a perpendicular axis of the first hole extending through the plate substantially perpendicular to the upper surface.

39. The bone plate of claim 38, wherein the first hole axis and the perpendicular axis intersect at an angle of between about 4° and 10°.

40. The bone plate of claim 38, wherein the first hole axis and perpendicular axis intersect at an angle of between about 13° and 17°.

41. The bone plate of claim 1, wherein the plate includes a plurality of first holes, the first hole axis of a first one of the first holes being non-parallel to the perpendicular axis of the first hole and extending at a first angle relative thereto, the first hole axis of a second one of the first holes being non-parallel to the perpendicular axis of the second first hole and extending at a second angle relative to the second hole perpendicular axis different from the first angle.

42. The bone plate of claim 41, wherein the first angle is between about 4° and 10° and the second angle is between about 13° and 17°.

43. The bone plate of claim 1, wherein a plurality of first holes are located along the longitudinal axis of the plate.

44. The bone plate of claim 43, wherein the plate is substantially straight.

45. The bone plate of claim 43, wherein the plate is curved, having a radius of curvature between about 80 mm to about 140 mm.

46. A bone plate system comprising:
a bone plate formed as a monolithic plate body with an upper surface and a lower surface including a first hole extending therethrough from the upper surface to the lower surface, the first hole including three regions separated from one another along a length of the first hole, first and third regions of the first hole being non-threaded, and a second middle region of the hole between the first and third regions including threading formed in a portion of the monolithic plate body forming a wall of the second region of the first hole, the threaded second region being configured and dimensioned to lock a mating fastener therein along a single, fixed first hole axis, wherein the second region is, in a direction from the upper surface to the lower surface, conically tapered inward and the third region is, in a direction from the upper surface to the lower surface, tapered outward, wherein the first region has, in a direction from the upper surface to the lower surface, a curved inward taper that is present around the axis of the first hole; and
a fastener to fasten the bone plate to a bone.

47. The bone plate of claim 46, wherein the first hole has a substantially circular cross section with a diameter.

48. The bone plate of claim 47, wherein the diameter of the circular cross section varies along the first hole axis.

49. The bone plate of claim 46, wherein the second region conically tapers at a cone angle of between about 5° and 15°.

50. The bone plate of claim 46, wherein a point of the second region nearest the lower surface abuts a point of the third region nearest the upper surface.

51. The bone plate of claim 46, wherein the third region is substantially smooth.

52. The bone plate of claim 46, wherein the third region conically tapers at a cone angle of between about 40° and 50°.

53. The bone plate of claim 46, further comprising at least one second hole, different from the first hole, formed in the monolithic plate body.

54. The bone plate of claim 53, wherein the second hole is elongated in a direction substantially parallel to a plane containing the upper surface of the plate and extends through the upper and lower surfaces.

55. The bone plate of claim 54, wherein the second hole is non-threaded and has an outer perimeter, at least a portion of the outer perimeter tapering inward from the upper surface to the lower surface of the plate to form at least one ramp surface for engagement with a head of the at least one fastener.

56. The bone plate of claim 54, the second hole having a center point and wherein the second hole includes a threaded portion and a non-threaded portion, and the threaded portion extends through an angle of between about 190° and about 280° with respect to the center point.

57. The bone plate of claim 54, wherein the plate body defines a longitudinal axis, and the second hole is elongated in a direction that is substantially aligned with the longitudinal axis.

58. The bone plate of claim 57, wherein the plate comprises at least two first holes and at least two second holes.

59. The bone plate of claim 46, wherein the bone plate extends along a longitudinal axis.

60. The bone plate of claim 59, wherein the bone plate has a straight portion extending along the longitudinal axis and a first curved portion at a first end thereof.

61. The bone plate of claim 60, wherein the plate includes a first end and a second end substantially opposite the first end, the plate including a second curved portion at the second end with the straight portion located between the first and second curved portions.

62. The bone plate of claim 61, wherein the first curved portion has a radius of curvature of about 50 mm.

63. The bone plate of claim 62, wherein two second holes are located adjacent to one another in the straight portion.

64. The bone plate of claim 61, wherein a first one of the first holes is located on the first curved portion, and a second one of the first holes is located on the second curved portion proximate the second end of the plate.

65. The bone plate of claim 46, wherein the first hole axis is not parallel to a perpendicular axis extending through the plate substantially perpendicular to the upper surface.

66. The bone plate of claim 65, wherein the first hole axis and the perpendicular axis intersect at an angle of between about 4° and 10°.

67. The bone plate of claim 65, wherein the first hole axis and the perpendicular axis intersect at an angle of between about 13° and 17°.

68. The bone plate of claim 46, wherein the plate includes a plurality of first holes, the first hole axis of a first one of the first holes being non-parallel to the perpendicular axis of the first hole and extending at a first angle relative thereto, the first hole axis of a second one of the first holes being non-parallel to the perpendicular axis of the second first hole and extending at a second angle relative to the second hole perpendicular axis different from the first angle.

69. The bone plate of claim 68, wherein the first angle is between about 4° and 10° and the second angle is between about 13° and 17°.

70. The bone plate of claim 46, wherein a plurality of first holes are located along the longitudinal axis of the plate.

71. The bone plate of claim 70, wherein the plate is substantially straight.

72. The bone plate of claim 70, wherein the plate is curved.

73. The bone plate of claim 72, wherein the plate is curved at a radius between about 80 mm to about 140 mm.

* * * * *